United States Patent [19]

Tjoeng et al.

[11] Patent Number: 5,624,956
[45] Date of Patent: Apr. 29, 1997

[54] UREA DERIVATIVES USEFUL AS PLATELET AGGREGATION INHIBITORS

[75] Inventors: Foe S. Tjoeng, Manchester; Mihaly V. Toth, St. Louis; Dudley E. McMackins, St. Charles, all of Mo.; Steven P. Adams, Andover, Mass.

[73] Assignee: The Monsanto Company, St. Louis, Mo.

[21] Appl. No.: 449,446

[22] Filed: May 24, 1995

Related U.S. Application Data

[62] Division of Ser. No. 202,148, Feb. 23, 1994, Pat. No. 5,475,025, which is a division of Ser. No. 9,526, Jan. 27, 1993, Pat. No. 5,314,902.

[51] Int. Cl.$^6$ .................. A61K 31/19; A61K 31/215; C07C 229/34; C07C 275/12
[52] U.S. Cl. .................. 514/535; 514/530; 514/531; 514/533; 514/534; 514/562; 514/563; 560/34; 562/439; 562/440
[58] Field of Search .................. 514/535, 538, 514/539, 562, 563, 530, 531, 533, 534; 560/34, 35; 562/439, 440

[56] References Cited

U.S. PATENT DOCUMENTS

| | | | |
|---|---|---|---|
| 4,570,006 | 2/1986 | Fuji et al. | 549/442 |
| 4,673,582 | 6/1987 | Nofre et al. | 426/548 |
| 4,873,253 | 10/1989 | Okamoto et al. | 514/352 |
| 4,954,512 | 9/1990 | Ogara et al. | 514/352 |
| 5,030,653 | 7/1991 | Trivedi | 514/510 |
| 5,039,805 | 8/1991 | Alig et al. | 546/224 |
| 5,086,069 | 2/1992 | Klein et al. | 514/399 |
| 5,220,050 | 6/1993 | Bovy et al. | 514/357 |
| 5,239,113 | 8/1993 | Bovy et al. | 562/440 |
| 5,254,573 | 10/1993 | Bovy et al. | 514/357 |
| 5,272,162 | 12/1993 | Tjoeng et al. | 514/344 |
| 5,344,837 | 9/1994 | Tjoeng et al. | 514/344 |
| 5,344,957 | 9/1994 | Bovy et al. | 560/35 |
| 5,354,738 | 10/1994 | Tjoeng et al. | 514/19 |
| 5,378,727 | 1/1995 | Bovy et al. | 514/465 |
| 5,409,939 | 4/1995 | Adams et al. | 514/335 |
| 5,424,334 | 6/1995 | Abood et al. | 514/562 |

FOREIGN PATENT DOCUMENTS

| | | |
|---|---|---|
| 301751 | of 1989 | European Pat. Off. . |
| 513810A1 | 11/1992 | European Pat. Off. . |
| WO92/15607 | 9/1992 | WIPO . |
| WO93/08164 | 4/1993 | WIPO . |
| WO93/12103 | 6/1993 | WIPO . |
| WO94/00424 | 1/1994 | WIPO . |
| WO94/22820 | 10/1994 | WIPO . |

*Primary Examiner*—Phyllis G. Spivak
*Attorney, Agent, or Firm*—Cynthia S. Kovacevic; Roger A. Williams

[57] ABSTRACT

Novel urea derivatives and pharmaceutical compositions thereof are provided which inhibit platelet aggregation.

9 Claims, No Drawings

UREA DERIVATIVES USEFUL AS PLATELET AGGREGATION INHIBITORS

This is a divisional application of application Ser. No. 08/202,148, filed on Feb. 23, 1994, now U.S. Pat. No. 5,475,025, which is a divisional of application Ser. No. 08/009,526, filed on Jan. 27, 1993, now issued as U.S. Pat. No. 5,314,902.

BACKGROUND OF THE INVENTION

1. Field of the Invention

This invention pertains to urea derivatives which inhibit platelet aggregation in mammals.

2. Related Art

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating or preventing platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. (See U.S. Pat. Nos. 4,517,686, 4,589,881, and 4,661,111). Certain relatively short peptide fragments from the same molecule were found to promote cell attachment to a substrate when immobilized on the substrate or to inhibit attachment when in a solubilized or suspended form. (See U.S. Pat. Nos. 4,578,079 and 4,614,517).

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Hayerstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses amidino or guanidinoaryl substituted alkanoic acid derivatives which inhibit protein to receptor binding and are useful for the treatment of thrombosis and cardiac infarction.

European Patent Application 372,486 discloses N-acyl beta amino acid derivatives of and their salts. Said compounds are useful for inhibiting platelet aggregation in the treatment of thrombosis, stroke, myocardial infarction, inflammation and arteriosclerosis, and for inhibiting metastasis.

European Patent Application 381,033 discloses amidino or guanidinoaryl substituted alkanoic acid derivatives useful for the treatment of thrombosis, apoplexy, cardiac infarction, inflammation, arteriosclerosis and tumors.

European Patent Application 445,796 discloses Acetic Acid derivatives useful as a ligand for adhesive proteins on platelets. As such these compounds are useful to modulate and/or inhibit platelet aggregation.

SUMMARY OF THE INVENTION

The present invention relates to a class of compounds represented by the formula:

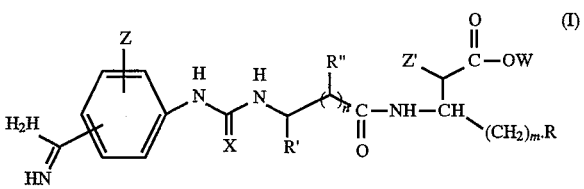

or a pharmaceutically acceptable salt thereof, wherein R is selected from the group consisting of hydrogen, lower alkyl radicals, lower alkenyl radicals, lower alkynyl radicals, alicyclic hydrocarbon radicals, and aromatic hydrocarbon radicals, wherein all of said radicals are optionally substituted with hydroxyl, lower alkoxy, lower alkyl, halogen, nitro, carboxyl, trifluoromethyl, amino, acyloxy, phenyl and naphthyl which are optionally substituted with halogen, nitro, lower alkoxy, and lower alkyl; or R is a monocyclic or bicyclic heterocyclyl radical in which 1 to about 3 heteroatoms are independently selected from oxygen, nitrogen and sulfur and which are optionally substituted with one or more groups selected from lower alkyl, lower alkoxy, halogen, and hydroxy;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

Z, Z' are independently selected from the group consisting of hydrogen, lower alkyl radicals, halogen, alkoxy, cyano, sulfonyl, and hydroxy radicals;

X is selected from the group consisting of oxygen, sulfur or nitrogen radicals, wherein nitrogen radicals may be substituted with hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

R', R" are independently selected from the group consisting of hydrogen, lower alkyl radicals, lower alkenyl radicals, lower alkynyl radicals, alicyclic hydrocarbon radicals, monocyclic or bicyclic aromatic hydrocarbon radicals, arylalkyl and monocyclic or bicyclic heterocyclyl radical in which 1 to about 3 heteroatoms are independently selected from oxygen, nitrogen and sulfur wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

m is an integer from 0 to about 6; and m is an integer 0 to about 3.

R is preferably selected from the group consisting of hydrogen, lower alkyl, lower alkenyl radicals, lower alkynyl radicals, pyridyl and 1,3-benzodioxole; more preferably pyridyl and 1,3-benzodioxole and hydrogen; even more preferably hydrogen.

W is preferably selected from the group consisting of hydrogen, lower alkyl, lower alkenyl radicals, lower alkynyl radicals; more preferably hydrogen.

Z, Z' is preferably selected from the group consisting of hydrogen and lower alkyl; more preferably hydrogen.

X is preferably selected from the group consisting of oxygen, sulfur or nitrogen radicals, wherein nitrogen radicals may be substituted with hydrogen or lower alkyl radicals.

R', R" are preferably selected from the group consisting of hydrogen, lower alkyl radicals, lower alkenyl radicals, monocyclic or bicyclic aromatic hydrocarbon radicals, and pyridyl; more preferably hydrogen, monocyclic aromatic hydrocarbon radicals and pyridyl.

m is an integer preferably 0 to about 3, more preferably 0 to about 2; most preferably 0.

n is an integer preferably 0 to about 2, more preferably 0 to about 1.

The invention further relates to pharmaceutical compositions comprising a compound of Formula (1). Such compounds and compositions have usefulness as inhibitors of platelet aggregation.

It is still another object of the invention to provide a method to therapeutically inhibit or modulate platelet aggregation or the like in a mammal in need of such treatment with a compound of the formula I in unit dosage form. Particularly in inhibiting or modulating platelet aggregation by administering an amount between 0.5 mg/kg to 10 mg/kg, preferably 3 mg/kg to an animal in need thereof.

Many other objects and purposes of the invention will be clear from the following detailed description of the invention and examples.

DETAILED DESCRIPTION OF THE INVENTION

A preferred embodiment of the present invention is a compound of the formula I or a pharmaceutically acceptable salt thereof:

wherein R is selected from the group consisting of hydrogen, lower alkyl radicals of 1 to about 6 carbon atoms, lower alkenyl radicals of 2 to about 8 carbon atoms, alicyclic hydrocarbon radicals of 3 to about 6 carbon atoms, monocyclic or bicyclic aromatic hydrocarbon radicals, and monocyclic or bicyclic heterocyclyl radical in which 1 to about 3 heteroatoms are independently selected from oxygen and nitrogen wherein all of said radicals are optionally substituted with hydroxyl, lower alkoxy, lower alkyl, halogen, nitro, carboxyl, and trifluoromethyl;

W is selected from the group consisting of hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, alkoxy, cyano, sulfonyl, lower alkyl and hydroxy radicals;

X is selected from the group consisting of oxygen, sulfur or nitrogen radicals, wherein nitrogen radicals may be substituted with hydrogen, lower alkyl radicals, lower alkenyl radicals, lower alkynyl radicals, alicyclic hydrocarbon radicals and aromatic hydrocarbon radicals;

R', R" are independently selected from the group consisting of hydrogen, lower alkyl radicals, lower alkenyl radicals, lower alkynyl radicals, alicyclic hydrocarbon radicals, monocyclic or bicyclic aromatic carbon radicals, arylalkyl and monocyclic or bicyclic heterocyclyl radical in which 1 to about 3 heteroatoms are independently selected from oxygen and nitrogen wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

m is an integer from 0 to about 6; and n is an integer 0 to about 3.

Another preferred embodiment of the present invention is a compound of the formula I or a pharmaceutically acceptable salt thereof:

wherein R is selected from the group consisting of hydrogen, lower alkyl radicals, phenyl radicals, and substituted phenyl radicals wherein each substituent are selected from the group consisting of lower alkyl, halogen, and carboxyl;

W is selected from the group consisting of hydrogen, lower alkyl radicals and lower alkenyl radicals;

Z, Z' are independently selected from the group consisting of hydrogen, halogen, alkoxy, and lower alkyl radicals;

X is selected from the group consisting of oxygen, sulfur or nitrogen radicals, wherein nitrogen radicals may be substituted with hydrogen, lower alkyl radicals, and alicyclic hydrocarbon radicals;

R', R" are independently selected from the group consisting of hydrogen, lower alkyl radicals, alicyclic hydrocarbon radicals, monocyclic or bicyclic aromatic carbon radicals, arylalkyl and pyridyl radicals wherein all of said radicals are optionally substituted with hydroxyl, lower alkyl, lower alkoxy, halogen, and nitro;

m is an integer from 0 to about 4; and n is an integer 0 to about 2.

Still another preferred embodiment of the present invention is a compound of the formula I or a pharmaceutically acceptable salt thereof:

wherein R is a monocyclic or bicyclic heterocyclyl radical in which 1 to about 3 heteroatoms are independently selected from oxygen and nitrogen wherein all of said radicals are optionally substituted with alkyl having 1 to 6 carbon atoms, alkoxy having 1 to 6 carbon atoms, halo, and hydroxy;

W is selected from the group consisting of hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, alkoxy, cyano, sulfonyl, lower alkyl and hydroxy radicals;

X is selected from the group consisting of oxygen, sulfur or nitrogen radicals, wherein nitrogen radicals may be substituted with hydrogen, lower alkyl radicals, lower alkenyl radicals, lower alkynyl radicals, alicyclic hydrocarbon radicals and aromatic hydrocarbon radicals;

R', R" are independently selected from the group consisting of hydrogen, lower alkyl radicals, lower alkenyl radicals, lower alkynyl radicals, alicyclic hydrocarbon radicals, monocyclic or bicyclic aromatic carbon radicals, arylalkyl and heterocyclyl radical in which 1 to about 3 heteroatoms are independently selected from oxygen and nitrogen wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

m is an integer from 0 to about 4; and n is an integer 0 to about 2.

Still another preferred embodiment of the present invention is a compound of the formula I or a pharmaceutically acceptable salt thereof: wherein R is selected from hydrogen, pyridyl, and 1,3-benzodioxole;

W is selected from the group consisting of hydrogen, and lower alkyl radicals;

Z, Z' are hydrogen;

X is selected from the group consisting of oxygen, sulfur or nitrogen radicals, wherein nitrogen radicals may be substituted with hydrogen, and lower alkyl radicals;

R', R" are independently selected from the group consisting of hydrogen, lower alkyl radicals and monocyclic or bicyclic aromatic hydrocarbon radicals;

m is an integer 0 to about 1; and n is an integer 0 to about 1.

As utilized herein, the term "lower alkyl" alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, hexen-2-yl, hexen-3-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" means a aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "lower alkoxy" alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, isobutoxy, sec-butoxy, tert-butoxy and the like.

The term "heterocyclyl radical" means a heterocyclyl hydrocarbon radical preferably an aromatic heterocyclyl hydrocarbon radical with 4 to about 10 carbon atoms, preferably about 5 to about 6; wherein 1 to about 3 carbon atoms are replaced by nitrogen, oxygen or sulfur. The "heterocyclyl radical" may be fused to a aromatic hydrocarbon radical or to another heterocyclyl radical. The "heterocyclyl radical" may be saturated, partially saturated, or fully unsaturated. Suitable examples include pyrrolyl, pyridinyl, pyrazolyl, pyrrolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolidinyl, 1,3-dioxolanyl, 2-imidazolinyl, imidazolidinyl, 2-pyrazolinyl, pyrazolidinyl, isoxazolyn, isothiazolyn, 1,2,3-oxadiazolyn, 1,2,3-triazolyn, 1,3,4-thiadiazolyn, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyn, quinolinyl, and the like.

The term "halogen" means fluorine, chlorine, bromine or iodine.

The term "pharmaceutically acceptable salt" refers to a salt prepared by contacting a compound of formula (I), with an acid whose anion is generally considered suitable for human consumption. Examples of pharmacologically acceptable salts include the hydrochloride, hydrobromide, hydroiodide, sulfate, phosphate, acetate, propionate, lactate, maleate, oxalate, malate, succinate, tartrate and citrate salts. All of these salts may be prepared by conventional means by reacting, for example, the appropriate acid with the corresponding compound of formula I.

Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine.

Total daily dose administered to a host in single or divided doses may be in amounts, for example, from 0.001 to 100 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more active pharmaceutical agents. When administered as a combination, the therapeutic agents can be formulated as separate compositions which are given at the same time or different times, or the therapeutic agents can be given as a single composition.

In the structures and formulas herein, the bond drawn across a bond of an aromatic ring can be to any available atom on the aromatic ring.

The compounds of formula I can exist in various isomeric forms and all such isomeric forms are meant to be included. Tautomeric forms are also included in the invention. Pharmaceutically acceptable salts of such isomers and tautomers are meant to be included as well.

Contemplated equivalents of the general formulas set forth above for the platelet aggregation inhibitors and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a halogen, hydroxy, amino and the like functional group, is not critical so long as it does not adversely affect the overall activity and/or synthesis procedure.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

The compounds listed above may be prepared by standard synthetic methods combined with methods analogous to solution phase peptide synthesis [see: The Peptides: Analysis, Synthesis, Biology (E. Gross and J. Meienhofer, eds.), (Vol. 1–5, Academic Press, N.Y.)], the disclosure of which is hereby incorporated by reference.

Purification of final compounds can be performed by reverse phase high pressure liquid chromatography [*High Performance Liquid Chromatography Protein and Peptide Chemistry*, F. Lottspeich, A. Henscher, K. P. Hupe, eds.) Walter DeGruyter, N.Y., 1981, the disclosure of which is hereby incorporated by reference.) or crystallization.

General synthetic sequences for preparing the compounds of formula I are outlined in scheme I–VII.

SCHEME I

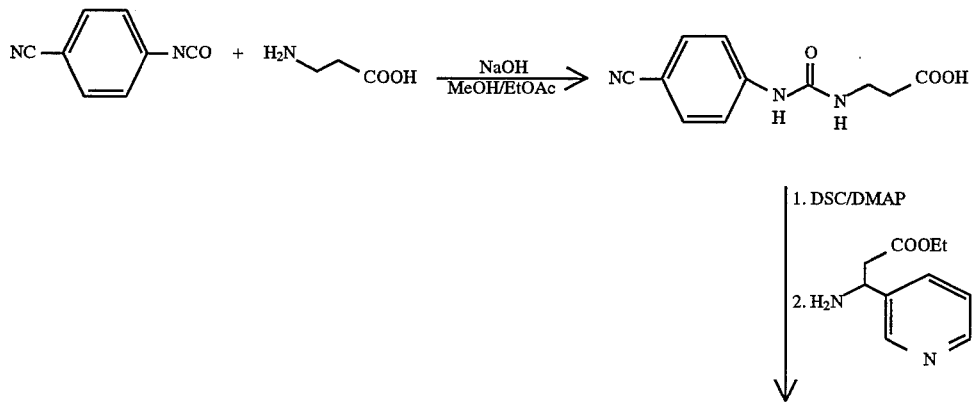

-continued
SCHEME I
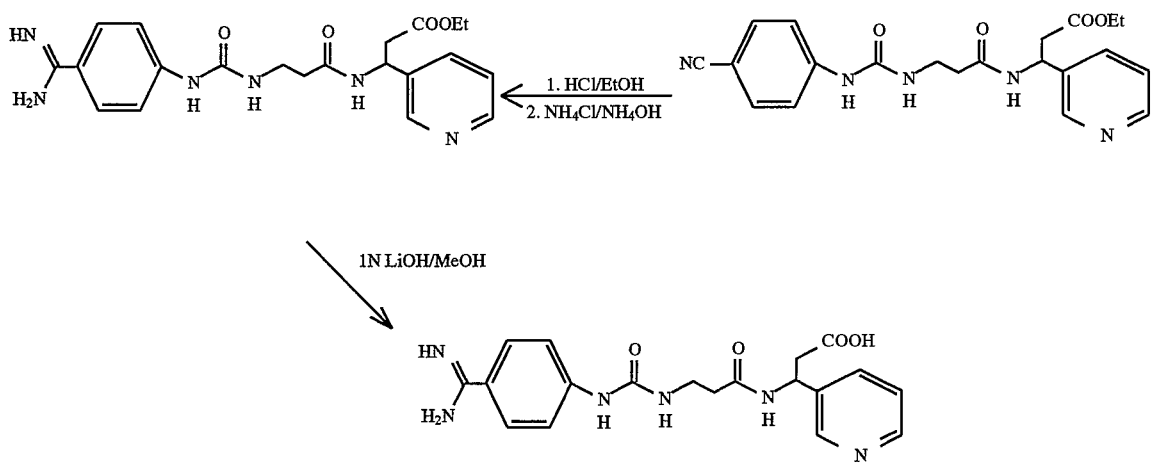
SCHEME II
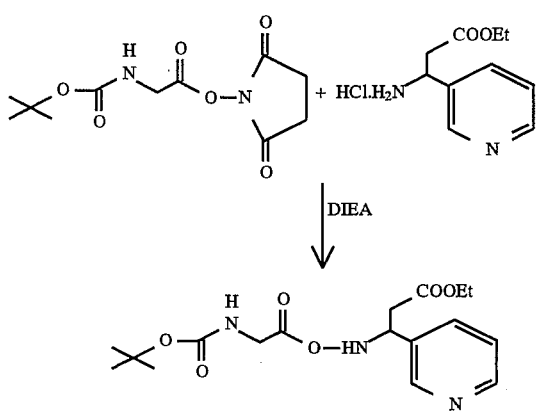
SCHEME III
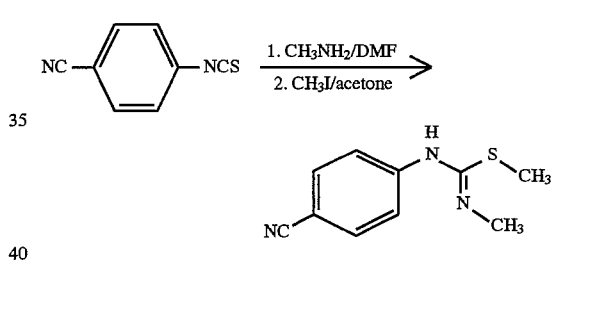
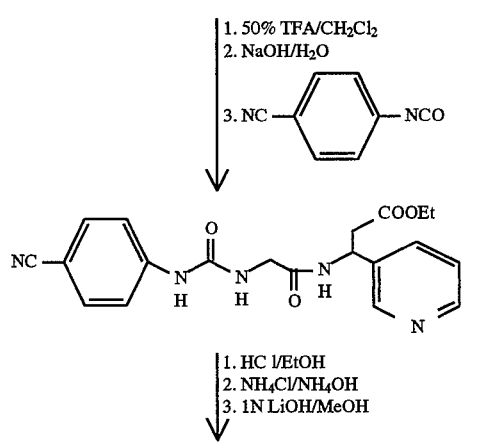
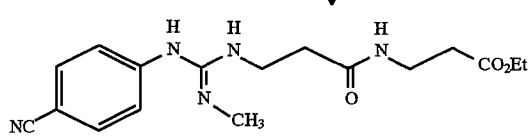
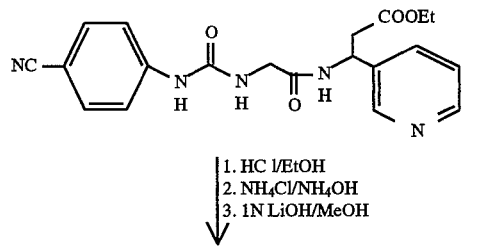
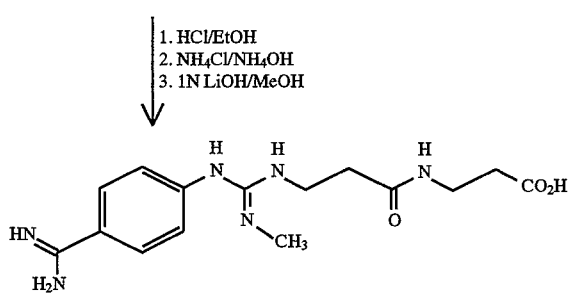

11
SCHEME IV
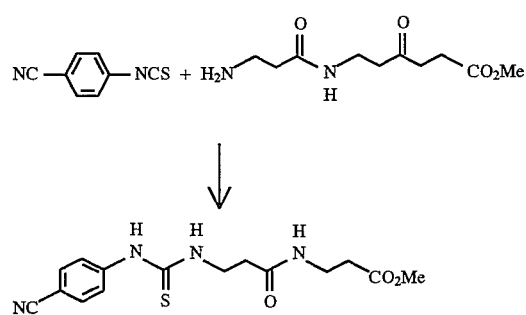
12
-continued
SCHEME IV
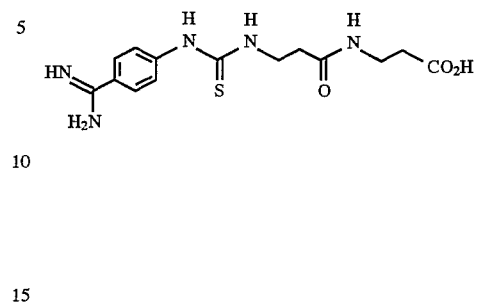
SCHEME V
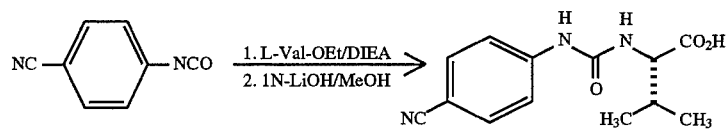
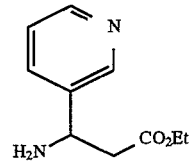
BOP/DIEA
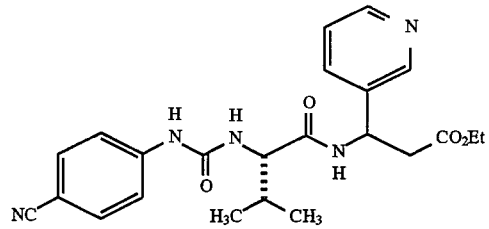
1. HCl/EtOH
2. NH₄Cl/NH₄OH
3. Diastereomers Separation
4. 1N LiOH/MeOH
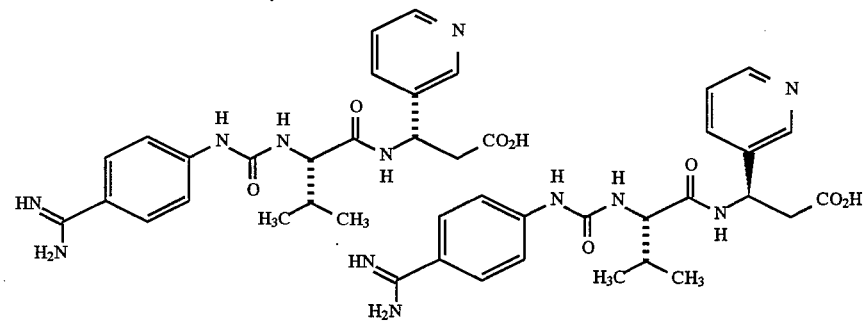

SCHEME VI
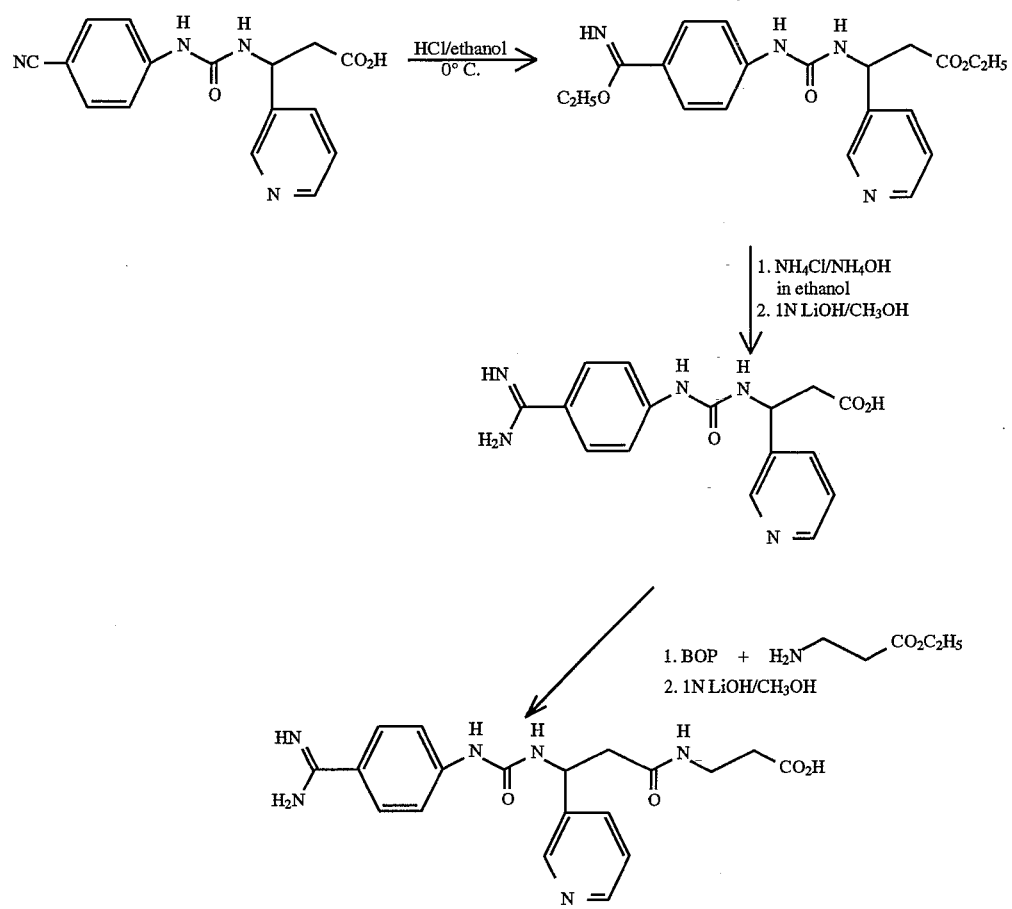
40
SCHEME VII
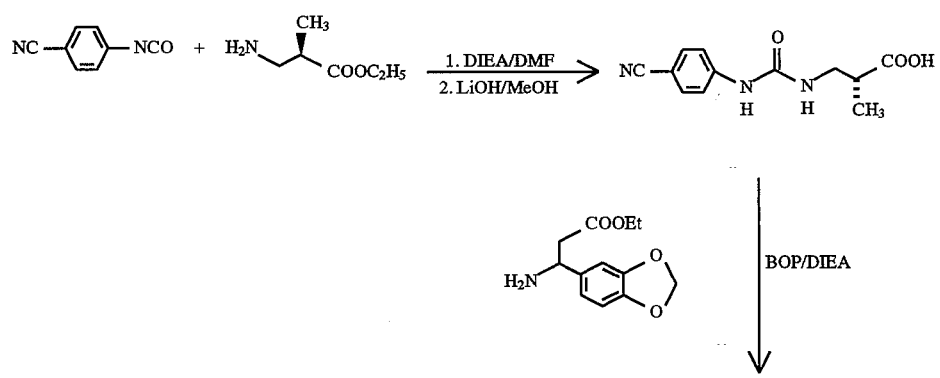

-continued
SCHEME VII

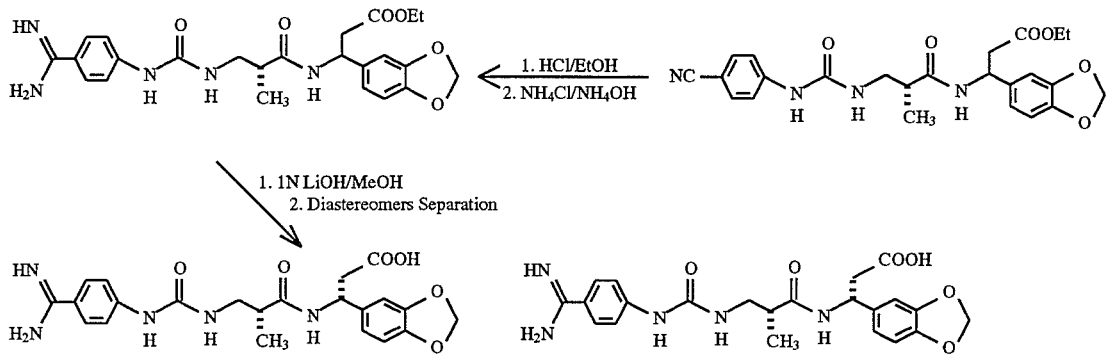

The following examples were made using the general outline as discussed above and are provided to illustrate the present invention and are not intended to limit the scope thereof. Those skilled in the art will readily understand that known variations of the conditions and processes of the following preparative procedures can be used to prepare these compounds. All temperatures expressed are in degrees centigrade.

EXAMPLE 1

Ethyl β-[[3-[[[4-aminoiminomethyl)phenyl]amino]-carbonyl]aminopropanoyl]-amino]-3-pyridinepropanoate.

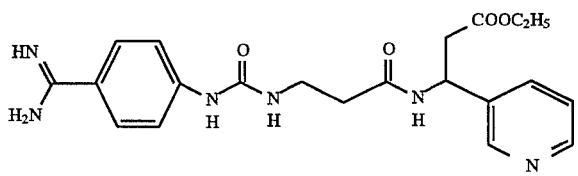

Step 1. Preparation of β-[[[(4-cyanophenyl)amino]-carbonyl]amino]propanoic acid.

Under a nitrogen blanket, a mixture of β-alanine (4.4 g; 49 mmoles), sodium hydroxide (2.0 g; 50 mmoles) and methanol (300 ml) was added rapidly to a suspension of 4-cyanophenylisocyanate (8.0 g; 55 mmoles) in ethyl acetate (300 ml). The mixture was stirred at 40° C. for 15 hrs and the volume was reduced to about 150 ml by distillation at reduced pressure. The solid was filtered off, washed with ethyl acetate and dried to yield 7 g of crude product. FAB-MS: MH+=232.

Step 2. Preparation of ethyl β-[[3-[[[4-aminoiminomethyl)phenyl]amino]carbonyl]aminopropanoyl]amino]-3-pyridinepropanoate.

Under a nitrogen blanket, a mixture of β-[[[(4-cyanophenyl)amino]carbonyl]-amino]propanoic acid (2.55 g; 10 mmoles), dry N,N-dimethylformamide (25 ml), 4N HCl in dioxane (2.2 ml), disuccinimidyl carbonate (3.1 g; 12 mmoles) and 4-dimethylaminopyridine (0.1 g) were stirred for 2hr at room temperature. In a separate flask, a mixture of ethyl β-[amino-(3-pyridyl)]propanoate dihydrochloride (2.7 g; 10 mmoles) and N,N-diisopropylethylamine (3 ml) was dissolved in dry N,N-dimethylformamide (20 ml). Both mixtures were combined and the stirring continued overnight. Solvents were removed under reduced pressure and the remaining crude coupling product was redissolved in dry ethanol (200 ml). The solution was saturated with dry HCl gas at 0° C. and was allowed to warm to room temperature.

After stirring for 1 hr, the ethanol was removed under reduced pressure and the residue was dissolved in ethanol (300 ml). The well-stirred solution was treated quickly with ammonium chloride (1 g) and aqueous ammonium hydroxide (10 ml). The reaction mixture was then taken down to dryness on rotaevaporator and the crude ester was purified by HPLC (C-18 DeltaPak column) using acetonitrile/water/trifluoroacetic acid. The desired fractions were collected and lyophilized. The residue was dissolved in about a two-fold molar excess of 0.1M aqueous HCl and the resulting solution was lyophilized to give a white solid. FAB-MS: MH+= 427. $^1$H-NMR (DMSO-d$_6$) δ 1.13 (t, 3H, CH$_2$CH$_3$), 2.37 (t, 2H, CH$_2$C$_2$CO), 2.95 (d,2H,CH(Py)CH$_2$CO), 3.30 (br d, 2H, NHCH$_2$CH$_2$), 4.03 (q, 2H, CH$_2$CH$_3$), 5.36 (m, 1H, NHCH(Py)CH$_2$), 6.71 (br t, 1H, CONHCH$_2$), 7.68 (q, 4H, Ar), 7.93 (m, 1H, Py), 8.46 (br d, CONHCH(Py)CH$_2$), 8.75–9.00 (m, 3H, Py), 8.90 and 9.16 (s, 4H, H$_2$NCNH$_2$+), 9.64 (s, 1H, ArNHCO).

Elemental Analysis: C$_{21}$H$_{26}$N$_6$O$_4$·2HCl·2H$_2$O

|  | C | H | N |
|---|---|---|---|
| Calculated: | 47.10 | 5.27 | 15.70 |
| Found: | 48.16 | 5.43 | 16.02 |

EXAMPLE 2

β-[[3-[[[4-aminoiminomethyl)phenyl]amino]-carbonyl]aminopropanoyl]amino]-3-pyridinepropanoic acid

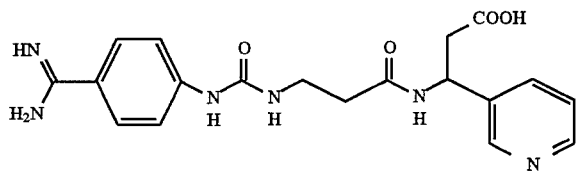

A portion of ethyl β-[[3-[[[4-(aminoiminomethyl)phenyl]amino]carbonyl]aminopropanoyl]amino]3-pyridinepropanoate (100 mg) was treated with 1N lithium hydroxide in methanol/water (1:1; 10 ml) for 2 hrs. The solution was adjusted to pH 5 with trifluoroacetic acid. The solvents were evaporated under reduced pressure. The residue was dissolved in water/acetonitrile and the crude product was purified by HPLC (C-18 DeltaPak column) using acetonitrile/water/trifluoro-acetic acid. The appropriate fractions were lyophilized and the residue was dissolved in 4–5 equivalents of 0.1M aqueous HCl. This solution was lyophilized to give a white powder. FAB-MS: MH+=399. $^1$H-NMR (DMSO-d$_6$) δ 2.37 (t, 2H CH$_2$CH$_2$CO), 2.91 (d, 2H, CH(Py)CH$_2$CO), 3.29 (br t, 2H, NHCH$_2$CH$_2$), 5.32 (m, 1H, NHCH(Py)CH$_2$), 6.76 (m, 1H, CONHCH$_2$), 7.68 (q, 4H, Ar), 8.04 (m, 1H, Py), 8.60 (d, 1H, CONHCH(Py)CH$_2$), 8.75–9.00 (m, 3H, Py), 9.03 and 9.17 (s, 4H$_2$NCNH$_2$+), 9.75 (s, 1H, ArNHCO).

Elemental Analysis: C$_{19}$H$_{22}$N$_6$O$_4$·3HCl·2H$_2$O

|  | C | H | N |
|---|---|---|---|
| Calculated: | 39.76 | 5.09 | 14.64 |
| Found: | 41.07 | 4.92 | 14.60 |

EXAMPLE 3

Ethyl β-[[[[[4-aminoiminomethyl)phenyl]amino]-carbonyl]aminoacetoyl]amino]-3-pyridinepropanoate.

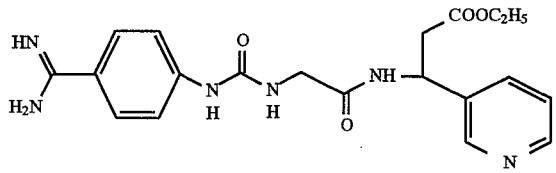

Under a nitrogen atmosphere, a mixture of N-t-Boc-glycine N-hydroxysuccinimide ester (2.7 g; 10 mmoles), ethyl β-[3-amino-(3-pyridyl)]propanoate dihydrochloride (2.7 g; 10 mmoles) and N,N-diisopropylethylamine (2 ml) were stirred in N,N-dimethylformamide (10 ml) for about 1 hr. Additional N,N-diisopropylethylamine was added to increase the pH to 6–7. The mixture was allowed to stir overnight and then was evaporated at reduced pressure. The residue was treated with trifluoroacetic acid/methylene chloride (1:1; 100 ml) for 2 hrs and evaporated under reduced pressure. The residue was dissolved in water and the solution ph was adjusted to 10. The water was then evaporated at reduced pressure. The dried residue was dissolved in methanol (100 ml) and added to a stirred suspension of 4-cyanophenylisocyanate (1.15 g; 7.9 mmoles). After stirring overnight at 40° C., the clear reaction solution was evaporated to dryness. The residue was purified by HPLC (C-18 DeltaPak column). The purified intermediate was dissolved in dry ethanol and the solution was bubbled with dry hydrogen chloride to saturation in an ice bath. The solution was allowed to warm to room temperature and evaporated under reduced pressure to give the crude imidate as a residue. This residue was dissolved in ethanol and treated with a solution of ammonium chloride (1 g) in ammonium hydroxide (7 ml). The reaction was warmed to 60° C. for 2 hrs, cooled and evaporated under reduced pressure to give the desired product. The crude product was purified by HPLC (DeltaPac C-18 column) using acetonitrile/water/trifluoroacetic acid. The lyophilized product was dissolved in water, treated with two equivalents of HCl and re-lyophilized to give the product as the hydrochloride salt of the amidine. FAB-MS: MH+=413. $^1$H-NMR (DMSO-d$_6$) δ1.12 (t, 3H, CH$_2$ CH$_3$), 2.96 (d, 2H, CHCH$_2$CO$_2$), 3.78 (br d, 2H, NHCH$_2$CONH), 4.04 (q, 2H, CO$_2$CH$_2$CH$_3$), 5.37 (q, 1H, NHCH(Py)CH$_2$), 6.84 (br t, 1H, CONHCH$_2$), 7.68 (q, 4H, Ar), 7.88 (q, 1H, Py), 8.41 (br d, 1H, CONHCH(Py)CH$_2$), 8.72–8.89 (m, 3H, Py), 8.97 and 9.16 (br s, 4H, H$_2$NCHNH$_2$+), 9.81 (s, 1H, ArNHCO).

Elemental Analysis: C$_{20}$H$_{24}$N$_6$O$_4$·3HCl·H$_2$O

|  | C | H | N |
|---|---|---|---|
| Calculated: | 44.49 | 5.41 | 15.57 |
| Found: | 45.63 | 4.87 | 15.27 |

EXAMPLE 4

β-[[[[[4-aminoiminomethyl)phenyl]amino]-carbonyl]aminoacetoyl]amino]-3-pyridinepropanoic acid

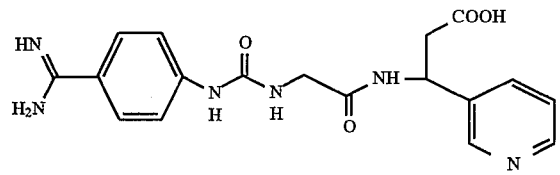

A portion of the ester (100 mg) was treated with 1N lithium hydroxide in methanol/water (1:1; 10 ml) for 30 min. The reaction mixture was adjusted to pH 5 with trifluoroacetic acid and taken down to dryness. The residue was then purified by HPLC (C-18 DeltaPak column) using acetonitrile/water/trifluoroacetic acid. The desired fractions were lyophilized and the residue was dissolved in a twofold molar excess of 0.1 M aqueous HCl. This solution was lyophilized to give a 70 mg of white solid. FAB-MS: MH+=385. $^1$H-NMR (DMSO-d$_6$) δ 2.87 (d, 2H, CHCH$_2$CO$_2$), 3.79 (d, 2H, NHCH$_2$CONH), 5.30 (g, 1H, NHCH(Py)CH$_2$), 6.80 (br t, 1H, CONHCH$_2$), 7.68 (q, 4H, Ar), 7.78 (m, 1H, Py), 8.28 (br d, 1H), CONHCH(Py)CH$_2$), 8.64–8.83 (m, 3H, Py), 8.93 and 9.14 (s, 4H$_2$NCHNH$_2$+), 9.77 (s, 1H, ArNMCO).

Elemental Analysis: C$_{18}$H$_{20}$N$_6$O$_4$·2HCl·H$_2$O

|  | C | H | N |
|---|---|---|---|
| Calculated: | 45.60 | 4.89 | 17.72 |
| Found: | 45.53 | 4.65 | 17.52 |

EXAMPLE 5

Ethyl β-[[3-[[[4-(aminoiminomethyl)phenyl]amino]N-methylcarbonylimide]aminopropanoyl]amino]propanoate

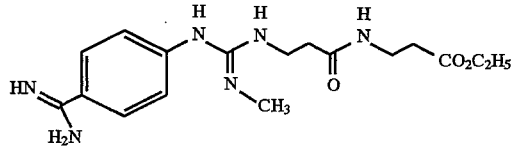

Step 1. Preparation of N-(4-cyanophenyl)-N,S-dimethylthiourea:

4-cyanophenylisothiocyanate (1.6 g; 10 mmoles) and methylamine (40% in water; 0.86 ml; 10 mmoles) were stirred in N,N-dimethylformamide (20 ml) at room temperature for 30 min. N,N-dimethylformamide was evaporated in vacuo and the residue was dissolved in acetone (20 ml). Iodomethane (0.62 ml; 10 mmoles) was added and after 1 hr stirring at reflux the same amount of iodomethane was added to the mixture. The stirring was continued overnight at room temperature. Acetone was evaporated under reduced pressure. N-(4-cyanophenyl)-N,S-dimethylthiourea was precipitated with water and collected by filtration as solid. Yield 1.9 g (95%). FAB-MS: MH+=206.2.

Step 2. Preparation of ethyl β-[[3-[[[4-(aminoiminomethyl) phenyl]amino]N-methylcarbonylimide]aminopropanoyl] amino]propanoate.

N-(4-cyanophenyl)-N,S-dimethylthiourea (4.1 g; 20 mmoles) was dissolved in ethanol (50 ml). β-Alanine (2.67 g; 30 mmoles) and 1N sodium hydroxide (30 ml) were added to the solution. The reaction mixture was then stirred at reflux for 12 hrs. Ethanol was removed in vacuo and the pH was adjusted to 5 by addition of acetic acid. N-(4-cyanophenyl)-N-methyl-N-(2-carboxyethyl)guanidine was isolated on HPLC using an acetonitrile, water/trifluoroacetic acid gradient. Yield: 3.9 g (81%). FAB-MS: MH$^+$=247.0. N-4-(cyanophenyl)-N-methyl-N-3-(carboxyethyl)-guanidine (0.5 g; 2 mmoles) and β-alanine ethyl ester (0.3 g; 2 mmoles) were dissolved in N,N-dimethylformamide (20 ml). To this mixture, benzotriazol-1-yl-oxy-tris (dimethylamino)phosphonium-hexafluorophosphate (0.88 g; 2 mmoles) and diisopropylethylamine (0.7 ml; 4 mmoles) were added. After 1 hr of stirring at room temperature, the reaction mixture was taken down to dryness. The remaining oil was dissolved in ethanol (30 ml) and treated with HCl gas at room temperature for 12 hrs. Ethanol was then removed and the residue was redissolved in ethanol(25 ml) and treated with ammonium chloride(1 g) in ammonium hydroxide solution (10 ml). After 4 hrs reaction, ethanol was evaporated, the pH of the remaining solution was adjusted to 5 with 50% acetic acid. The product was purified by HPLC (C-18 DeltaPak column) using acetonitrile/water/ trifluoroacetic acid to yield 173 mg of white solid (24%). FAB-MS: MH$^+$=363.0.

EXAMPLE 6

β-[[3-[[[4-(aminoiminomethyl)phenyl]amino]N-methylcarbonylimide]aminopropanoyl]amino]propanoic acid.

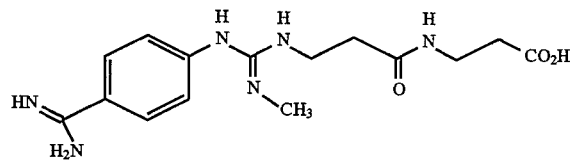

Ethyl β-[[3-[[[4-aminoiminomethyl)phenyl]amino]N-methylcarbonylimide]aminopropanoyl]amino]-propanoate (100 mg; 0.2 mmoles) was dissolved in methanol (10 ml) and hydrolyzed with 1N lithium hydroxide (10 ml) for 10 min. Methanol was evaporated and the pH of the remaining solution was adjusted to 5 with 50% acetic acid. The product was isolated on C-18 DeltaPak HPLC column using a 30 min linear gradient of 0–30% acetonitrile/water/0.05% trifluoroacetic acid and it was eluted at 14% acetonitrile concentration. The desired fractions were collected and lyophilized to yield 40 mg (44%) of white, hygroscopic material. FAB-MS: MH$^+$=335.2.

Elemental analysis: $C_{15}H_{22}N_6O_3 \cdot 2CF_3COOH$

|  | C | H | N |
|---|---|---|---|
| Calculated: | 39.31 | 4.48 | 14.48 |
| Found: | 39.90 | 4.25 | 14.60 |

EXAMPLE 7

Ethyl β-[[3-[[[4(aminoiminomethyl)phenyl]amino]-thiocarbonyl]aminopropanoyl]amino]propanoate.

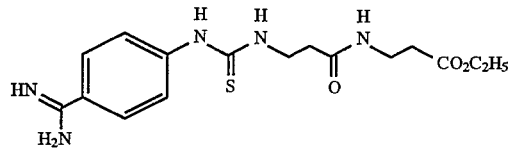

4-cyanophenylisothiocyanate (0.16 g; 1 mmol) was reacted with β-Ala-β-Ala-OMe (0.3 g; 1 mmol) in N,N-dimethylformamide (10 ml) in the presence of diisopropylethylamine (0.175 ml; 1 mmol) for 30 min. After complete reaction, N,N-dimethylformamide was evaporated and the residue was dissolved in ethanol (15 ml). HCl gas was bubbled into the solution in ice bath for 20 min. and the mixture was stirred at room temperature for 12 hrs. Ethanol was evaporated and the residue was redissoved in ethanol (10 ml) and treated with ammonium chloride in ammonium hydroxide (10 ml) at room temperature for 4 hrs. Yield: 190 mg (52%). FAB-MS: MH$^+$=366.2.

Elemental analysis: $C_{16}H_{23}N_5O_3S \cdot CF_3COOH$

|  | C | H | N |
|---|---|---|---|
| Calculated: | 43.42 | 5.22 | 14.07 |
| Found: | 44.83 | 4.88 | 14.34 |

EXAMPLE 8

β-[[3-[[[4(aminoiminomethyl)phenyl]amino]-thiocarbonyl] aminopropanoyl]amino]propanoic acid.

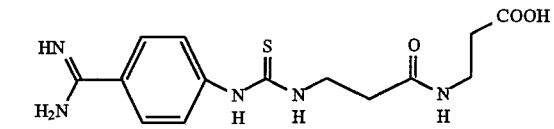

Ethyl β-[[3-[[[4(aminoiminomethyl)phenyl]-amino]thiocarbonyl]aminopropanoyl]amino]propanoate (65 mg; 0.18 mmoles) was treated in 1N lithium hydroxide/methanol (20 ml; 1:1) for 10 min. Methanol was evaporated and the pH of the remaining mixture was adjusted to 5 with 50% acetic acid. The mixture was then purified by HPLC using a linear gradient of acetonitrile/water/0.05% trifluoro-acetic acid (0–20% acetonitrile in 30 min). Yield: 51 mg (85%). FAB-MS: MH$^+$=338.0.

Elemental analysis: $C_{14}H_{19}N_5O_3S \cdot CF_3COO$

|  | C | H | N |
|---|---|---|---|
| Calculated: | 40.91 | 4.68 | 14.91 |
| Found: | 41.32 | 4.10 | 14.87 |

EXAMPLE 9

Ethyl β-[[[2(S)-[[[4(aminoiminomethyl)phenyl]-amino]carbonyl]amino]isobutanoyl]amino]-3-pyridinepropanoate.

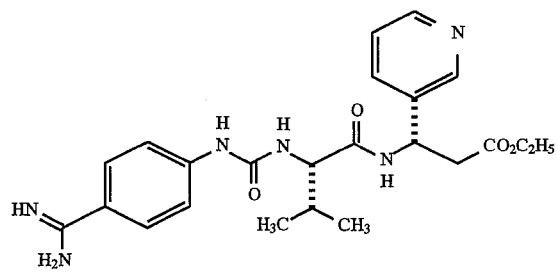

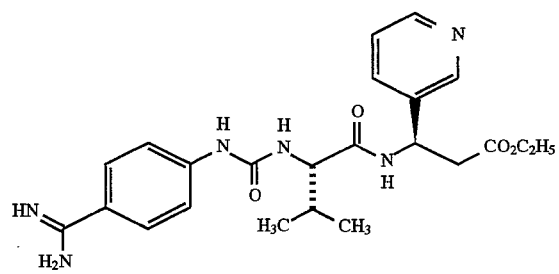

Step 1. Preparation of β(S)-[[[(4-cyanophenyl)amino]carbonyl]amino]isobutanoic acid.

4-cyanophenylisocyanate (0.29 g; 2 mmoles) was reacted with L-valine ethyl ester. HCl (0.36 g; 2 mmoles) in N,N-dimethylformamide (15 ml) in the presence of N,N-diisopropylethylamine (0.26 g; 2 mmoles) for 1 hr. The mixture was then treated with 1N lithium hydroxide (20 ml) for 30 min and N,N-dimethylformamide was removed under reduced pressure. The crude product was purified by HPLC using a linear gradient of acetonitrile/water/0.05% trifluoroacetic acid (10–50% acetonitrile in 30 min). Yield: 310 mg (59%). FAB-MS: MH$^+$=262.1.

Step 2. Preparation of ethyl β-[[[2(S)-[[[4-(aminoiminomethyl)phenyl]amino]carbonyl]amino]-isobutanoyl]amino]3-pyridinepropanoate.

β(S)-[[[(4-cyanophenyl)amino]carbonyl]-amino] isobutanoic acid (0.13 g; 0.5 mmoles) was coupled with ethyl β-[3-amino-(3-pyridyl)]propanoate hydrochloride (0.23 g; 1 mmol) in the presence of benzotriazol-1-yl-oxy-tris(dimethylamino)phosphonium-hexafluorophosphate (0.22 g; 0.5 mmoles) and N,N-diisopropylethylamine (0.13 g; 1 mmol) in N,N-dimethylformamide (15 ml) for 1 hr. N,N-dimethylformamide was evaporated and the residue was dissolved in ethanol (20 ml). The solution was cooled in an ice bath and bubbled with HCl gas for 30 min. The stirring was continued for 12 h at room temperature. Ethanol was removed under reduced pressure and the remaining oil was redissolved in ethanol (15 ml). The solution was treated with ammonium chloride (1 g) in ammonium hydroxide (10 ml) for 4 h at room temperature. Ethanol was removed on rotaevaporator and the residue was dissolved in water. The pH of the sample was adjusted to 5 with 50% acetic acid and the product was purified by HPLC using a linear gradient of acetonitrile/water/trifluoroacetic acid (0–30% acetonitrile in 30 min). Diastereomers were separated with an overall yield of 200 mg (88%). FAB-MS: MH$^+$=455.1 (isomer 1) and 455.2 (isomer 2).

EXAMPLE 10

β-[[[2(S)-[[[4(aminoiminomethyl)phenyl]amino]-carbonyl]amino]isobutanoyl]-amino]-3-pyridinepropanoic acid.

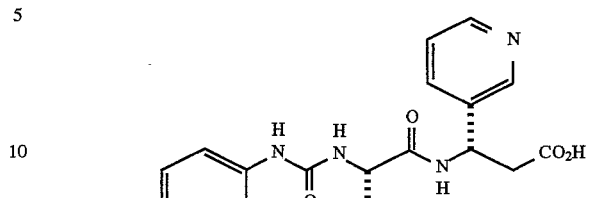

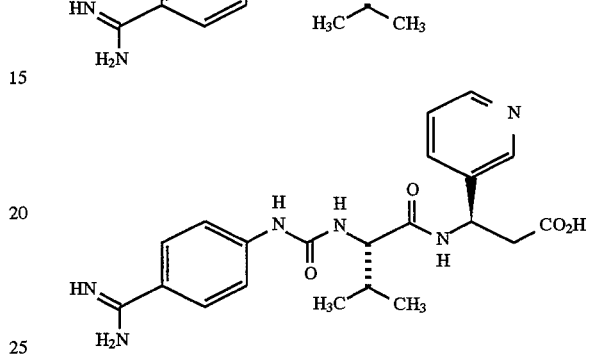

Ethyl β-[[[2(S)-[[[4(aminoiminomethyl)phenyl]-amino]carbonyl]amino]-isobutanoyl]amino]3-pyridinepropanoate. CF$_3$COOH (100 mg; isomer 1 and 2) was hydrolyzed separately in methanol (10 ml) and 1N lithium hydroxide (10 ml) for 10 min. Methanol was then evaporated under reduced pressure and the residue was dissolved in water. The pH of the solution was adjusted to 5 with 50% acetic acid. The crude material was then purified by HPLC using a linear gradient of acetonitrile/water/trifluoroacetic acid (0–30% acetonitrile in 30 min) as described above. Yield: 94 mg (isomer 1) and 76 mg (isomer 2). FAB-MS: MH$^+$=427.3. Elemental analysis: C$_{21}$H$_{26}$N$_6$O$_4$·2 CF$_3$COOH

|  | C | H | N |
|---|---|---|---|
| Calculated: | 44.64 | 4.46 | 12.50 |
| Found (isomer 1): | 44.57 | 4.03 | 12.49 |
| Found (isomer 2): | 44.54 | 4.03 | 12.57 |

Ethyl β-[[3-[[[[4(aminoiminomethyl)phenyl]-amino]carbonyl]amino](3-pyridine)propanoyl]amino]-propanoate.

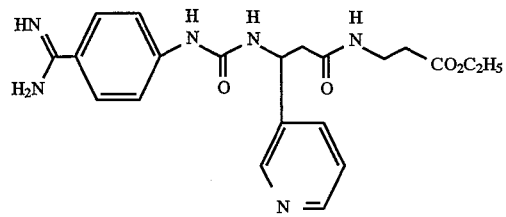

Step 1. Preparation of β-[[[[4-(aminoiminomethyl)phenyl]amino]carbonyl]amino]-3-pyridinepropanoic acid.

β-[[[(4-cyanophenyl)amino]carbonyl]amino]-3-pyridinepropanoic acid (1 g; 3.1 mmoles) was dissolved in ethanol (100 ml) and the solution was cooled in an ice bath. The mixture was bubbled with HCl gas for 45 min. and allowed to stand in the refrigerator overnight. The solvent was removed under reduced pressure and the residue was used without any further purification. This material (FAB-MS: MH$^+$=385) was then redissolved in ethanol (90 ml). To this solution, ammonium chloride (0.5 g) in ammonium hydroxide (3 ml) was added. The reaction mixture was heated up to reflux for 10 min. and stirred for 4 hr at room temperature. The mixture was then taken down to dryness on rotaevaporator and the residue was purified by HPLC (C-18 DeltaPak column) using acetonitrile/water/trifluoroacetic acid solvent system. The desired fractions were collected and lyphilized to give a white solid (0.72 g). FAB-MS: $MH^+=356$. A portion of this material (100 mg) was then treated with 1N lithium hydroxide in methanol/water (1:1; 10 ml) for ½ hr. The solvents were evaporated under reduced pressure and the residue was dissolved in water/acetonitrile. The crude product was purified by HPLC (C-18 DeltaPak column) using acetonitrile/water/trifluoroacetic acid. The desired fractions were lyophilized and the residue was dissolved in a twofold molar excess of 0.1M aqueous HCl. This solution was lyophilized to give 85 mg of white solid. FAB-MS: $MH^+=328$.

Elemental analysis: $C_{16}H_{17}N_5O_3 \cdot 2CF_3COOH \cdot H_2O$

|  | C | H | N |
|---|---|---|---|
| Calculated: | 40.58 | 3.91 | 11.83 |
| Found: | 40.85 | 3.33 | 11.69 |

Step 2. Preparation of ethyl β-[[3-[[[[4-(aminoiminomethyl) phenyl]amino]carbonyl]amino](3-pyridine)propanoyl] amino]propanoate.

β-[[[[4(aminoiminomethyl)phenyl]-amino]carbonyl] amino]-3-pyridinepropanoic acid. HCl (1 g; ~2.5 mmoles) was dissolved in N,N-dimethylformamide (20 ml). N,N-Diisopropylethylamine (0.52 g; 4 mmoles) and β-alanine ethylester. HCl (0.62 g; 4 mmoles) were added. To this mixture, benzotriazol-1-yl-oxy-tris(dimethylamino)-phosphonium hexafluorophosphate (1.32 g; 3 mmoles) and N,N-diisopropylethylamine (0.39 g; 3 mmoles) in N,N-dimethylformamide (20 ml) were added with stirring. The coupling was carried out overnight and the reaction mixture was then taken down to dryness on rotavapor. The crude product was purified by HPLC (C-18 DeltaPak column) using a linear gradient of acetonitrile/water/trifluoroacetic acid. The desired fractions were collected and lyophilized to give 410 mg of white solid. FAB-MS: $MH^+=427.5$.

Elemental analysis: $C_{21}H_{26}N_6O_4 \cdot 3CF_3COOH$

|  | C | H | N |
|---|---|---|---|
| Calculated: | 42.19 | 3.80 | 10.93 |
| Found: | 43.37 | 3.66 | 13.30 |

β-[[3-[[[[4-(aminoiminomethyl)phenyl]amino]-carbonyl] amino](3-pyridine)propanoyl]amino]-propanoic acid.

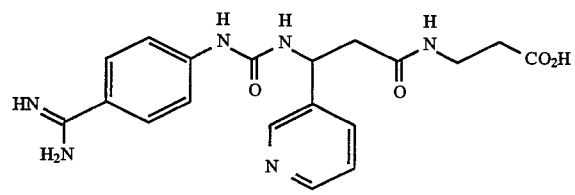

A portion of ethyl β-[[3-[[[[4-(aminoiminomethyl) phenyl]amino]carbonyl]amino](3-pyridine)propanoyl] amino]-propanoate (100 mg) was then treated with 1N lithium hydroxide in methanol/water (1:1; 10 ml) for 20 min. The solvents were evaporated under reduced pressure and the residue was dissolved in water/acetonitrile. The crude product was purified by HPLC (C-18 DeltaPak column) using acetonitrile/water/trifluoroacetic acid. The desired fractions were lyophilized and the residue was dissolved in a twofold molar excess of 0.1M aqueous HCl. This solution was lyophilized to give 65 mg of white solid. FAB-MS: $MH^+=399$.

Elemental analysis: $C_{19}H_{22}N_6O_4 \cdot 3CF_3COOH \cdot 3H_2O$

|  | C | H | N |
|---|---|---|---|
| Calculated: | 37.79 | 3.93 | 10.58 |
| Found: | 36.35 | 3.94 | 11.83 |

EXAMPLE 13

Ethyl β-[[2(R)-[[[[4-(aminoiminomethyl)phenyl]-amino]carbonyl]amino]methylpropanoyl]amino]-1,3-benzodioxole-5-propanoate.

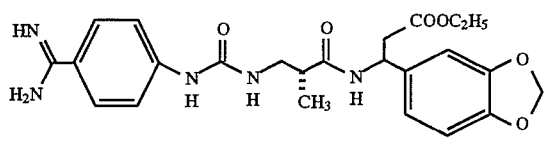

Step 1. Preparation of β-[[[[4(aminoiminomethyl)-phenyl] amino]carbonyl]amino](2R-methyl)propanoic acid.

4-cyanophenylisocyanate (0.29 g; 2 mmoles) was reacted with 2(R)-methyl-3-amino-propanoic acid ethyl ester. HCl (0.34 g; 2 mmoles) in N,N-dimethylformamide (15 ml) in the presence of N,N-diisopropylethylamine (0.26 g; 2 mmoles) for 12 hrs. The mixture was treated with 1N lithium hydroxide (10 ml) for 15 min and N,N-dimethylformamide was removed under reduced pressure. The crude product was purified by HPLC using a linear gradient of acetonitrile/water/0.05% trifluoroacetic acid. The desired fractions were collected and lyophilized to give 310 mg of white solid. (FAB-MS: $MH^+=246.1$).

Preparation of ethyl β-[[2(R)[[[[4-(aminoiminomethyl) phenyl]amino]carbonyl]-amino]methylpropanoyl]amino]-1, 3-benzodioxole-5-propanoate.

β-[[[[4(aminoiminomethyl)phenyl]-amino]carbonyl] amino]-2-methylpropanoic acid (0.12 g; 0.5 mmoles) was coupled with ethyl β(R)-[amino-(1,3-benzodioxole-5)]-propanoate hydrochloride (0.14 g; 0.5 mmoles) in the presence of benzotriazol-1-yl-oxy-tris(dimethylamino) phosphonium-hexafluorophosphate (0.22 g; 0.5 mmoles) and N,N-diisopropylethylamine (0.13 g; 1 mmol) in N,N-dimethylform-amide (15 ml) for 2 hrs. N,N-dimethylformamide was evaporated and the residue was dissolved in ethanol (50 ml). The solution was cooled in an ice bath and bubbled with HCl gas for 30 min. The stirring was continued for 12 h at room temperature. Ethanol was removed under reduced pressure and the remaining oil was redissolved in ethanol (15 ml). The solution was treated with ammonium chloride (1 g) in ammonium hydroxide (10 ml) for 4 h at room temperature. Ethanol was removed on rotaevaporator and the residue was dissolved in water. The pH was adjusted to 5 with 50% acetic acid and the material was purified by HPLC using a linear gradient of acetonitrile/water/trifluoroacetic acid. The desired fractions were collected and lyophilized to yield 180 mg (74%) of white material. FAB-MS: $MH^+=484.2$.

Elemental analysis: $C_{24}H_{29}N_5O_6 \cdot CF_3COOH \cdot H_2O$

|  | C | H | N |
|---|---|---|---|
| Calculated: | 50.73 | 5.20 | 11.38 |
| Found: | 51.32 | 5.00 | 11.51 |

EXAMPLE 14

β-[[2(R)-[[[[4(aminoiminomethyl)phenyl]-amino]carbonyl]amino]methyl-propanoyl]-amino]1,3-benzodioxole-5-propanoic acid.

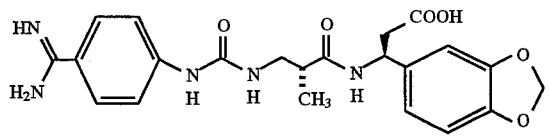

A portion of ethyl β-[[2(R)-[[[[4-(aminoiminomethyl)phenyl]amino]carbonyl]-amino]methylpropanoyl]amino]-1,3-benzodioxole-5-propanoate (0.18 g; 0.37 mmoles)) was then treated with 1N lithium hydroxide in methanol/water (1:1; 10 ml) for 15 min. The solvents were evaporated under reduced pressure and the residue was dissolved in water/acetonitrile. The crude product was purified by HPLC (C-18 DeltaPak column) using a gradient of acetonitrile/water/trifluoroacetic acid. Both diastereomers were separated and the desired fractions were lyophilized to give 121 mg of white solid (71% combined yield). FAB-MS: $MH^+$=456.3 (isomer 1) and 456.2 (isomer 2).

Elemental analysis: $C_{22}H_{25}N_5O_6 \cdot CF_3COOH \cdot H_2O$

|  | C | H | N |
|---|---|---|---|
| Calculated: | 49.06 | 4.77 | 11.92 |
| Found (isomer 1): | 48.62 | 4.39 | 11.76 |
| Found (isomer 2): | 49.12 | 4.31 | 11.86 |

Further examples included in this invention were made by the above described methods:

EXAMPLE 15

Ethyl β-[[3-[[[4(aminoiminomethyl)phenyl]amino]-carbonyl]aminopropanoyl]-amino]propanoate; FAB-MS: MH+= 350.

Elemental analysis: $C_{16}H_{23}N_5O_4$

|  | C | H | N |
|---|---|---|---|
| Calculated: | 47.58 | 6.48 | 17.34 |
| Found: | 46.54 | 6.11 | 16.97 |

EXAMPLE 16

β-[[3-[[[4(aminoiminomethyl)phenyl]amino]-carbonyl]aminopropanoyl]amino]-propanoic acid; FAB-MS: MH+= 322.

Elemental analysis: $C_{14}H_{19}N_5O_4 \cdot 5H_2O \cdot 2NaCl \cdot HCl$

|  | C | H | N |
|---|---|---|---|
| Calculated: | 29.77 | 5.35 | 12.40 |
| Found | 29.84 | 5.56 | 13.27 |

EXAMPLE 17

Ethyl β-[[3-[[[4(amino iminomethyl)-phenyl]amino]-carbonyl]aminoacetyl]-amino]1,3-benzodioxole-5-propanoate; FAB-MS: MH+=456.
Elemental analysis: $C_{22}H_{25}N_5O_6 \cdot H_2O \cdot HCl$

|  | C | H | N |
|---|---|---|---|
| Calculated: | 51.78 | 5.53 | 13.79 |
| Found | 50.86 | 5.13 | 13.33 |

EXAMPLE 18

β-[[3-[[[4(aminoiminomethyl)phenyl]amino]carbonyl]-aminoacetyl]amino]1,3-benzodioxole-5-propanoic acid; FAB-MS: MH+=428.
Elemental analysis: $C_{20}H_{21}N_5O_6 \cdot H_2O \cdot 2HCl$

|  | C | H | N |
|---|---|---|---|
| Calculated: | 46.34 | 4.86 | 13.51 |
| Found | 47.07 | 4.28 | 12.63 |

EXAMPLE 19

Ethyl β-[[3-[[[4(aminoiminomethyl)phenyl]amino]-thiocarbonyl]aminopropanoyl]-amino]-3-pyridinepropanoate; FAB-MS: MH+=443.

EXAMPLE 20

β-[[3-[[[(aminoiminomethyl)phenyl]amino]thiocarbonyl]-aminopropanoyl]amino]-3-pyridinepropanoic acid; FAB-MS: MH+=415.
Elemental analysis: $C_{19}H_{22}N_6O_3 \cdot 2CF_3COOH \cdot H_2O$

|  | C | H | N |
|---|---|---|---|
| Calculated: | 41.81 | 3.93 | 12.72 |
| Found | 41.02 | 3.76 | 12.97 |

EXAMPLE 21

Ethyl β-[[2(S)-[[[4(aminoiminomethyl)phenyl]amino]-carbonyl]aminopropanoyl]-amino]-3-pyridinepropanoate; FAB-MS: MH+=427.

EXAMPLE 22

β-[[2(S)-[[[4(aminoiminomethyl)phenyl]amino]-carbonyl]aminopropanoyl]amino]-3-pyridinepropanoic acid; FAB-MS: MH+=399.

EXAMPLE 23

Ethyl β-[[2(S)-[[[4-(aminoiminomethyl)phenyl]amino]-carbonyl]amino]hydroxy-propanoyl]amino]-3-pyridinepropanoate; FAB-MS: MH+=443.

Elemental analysis: $C_{21}H_{26}N_6O_5 \cdot 2CF_3COOH \cdot H_2O$

|  | C | H | N |
|---|---|---|---|
| Calculated: | 43.60 | 4.36 | 12.21 |
| Found: | 43.73 | 4.37 | 12.39 |

EXAMPLE 24

β-[[2(S)-[[[[4-(aminoiminomethyl)phenyl]amino]carbonyl]-amino]hydroxy-propanoyl]amino]-3-pyridinepropanoic acid; FAB-MS: MH+=415.

Elemental analysis: $C_{19}H_{22}N_6O_5 \cdot 2CF_3COOH \cdot H_2O$

|  | C | H | N |
|---|---|---|---|
| Calculated: | 41.81 | 3.93 | 12.72 |
| Found: | 41.13 | 3.50 | 12.59 |

EXAMPLE 25

Ethyl β-[[2(S)-[[[[4-(aminoiminomethyl)phenyl]amino]-carbonyl]amino]phenyl-acetoyl]amino]-3-pyridinepropanoate; FAB-MS: MH+=489.

EXAMPLE 26

β(S)-[[2(S)-[[[[4(aminoiminomethyl)phenyl]amino]-carbonyl]amino]phenylacetoyl]-amino]-3-pyridinepropanoic acid; FAB-MS: MH+=461.

Elemental analysis: $C_{24}H_{24}N_6O_4 \cdot 2CF_3COOH \cdot H_2O$

|  | C | H | N |
|---|---|---|---|
| Calculated: | 47.45 | 3.95 | 11.86 |
| Found: | 47.76 | 3.59 | 11.94 |

EXAMPLE 27

β(R)-[[2(S)-[[[[4(aminoiminomethyl)phenyl]amino]-carbonyl]amino]phenylacetoyl]-amino]-3-pyridinepropanoic acid; FAB-MS: MH+=461.

Elemental analysis: $C_{24}H_{24}N_6O_4 \cdot 2CF_3COOH \cdot H_2O$

|  | C | H | N |
|---|---|---|---|
| Calculated: | 47.45 | 3.95 | 11.86 |
| Found: | 47.52 | 3.37 | 12.02 |

EXAMPLE 28

Ethyl β-[[2(S)-[[[[4-(aminoiminomethyl)phenyl]amino]carbonyl]-amino]isobutyl-acetoyl]amino]-3-pyridinepropanoate; FAB-MS: MH+=469.

EXAMPLE 29

β(S)-[[2(S)-[[[[4-(aminoiminomethyl)phenyl]amino]carbonyl]-amino]isobutyl-acetoyl]amino]-3-pyridinepropanoic acid; FAB-MS: MH+=441.

Elemental analysis: $C_{22}H_{28}N_6O_4 \cdot CF_3COOH \cdot 2H_2O$

|  | C | H | N |
|---|---|---|---|
| Calculated: | 48.81 | 5.59 | 14.23 |
| Found: | 48.51 | 5.83 | 13.12 |

EXAMPLE 30

β(R)-[[2(S)-[[[[4-(aminoiminomethyl)phenyl]amino]carbonyl]-amino]isobutyl-acetoyl]amino]-3-pyridinepropanoic acid; FAB-MS: MH+=441.
Elemental analysis: $C_{22}H_{28}N6O_4 \cdot 2CF_3COOH \cdot H_2O$

|  | C | H | N |
|---|---|---|---|
| Calculated: | 45.48 | 4.66 | 12.24 |
| Found: | 45.22 | 4.50 | 12.45 |

EXAMPLE 31

Ethyl β-[[2(S)-[[[4-(aminoiminomethyl)phenyl]amino]carbonyl]-amino-3-(naphthyl-2)propanoyl]amino]-propanoate; FAB-MS: MH+=476.
Elemental analysis: $C_{26}H_{29}N_5O_4 \cdot CF_3COOH$

|  | C | H | N |
|---|---|---|---|
| Calculated: | 57.04 | 5.26 | 11.88 |
| Found: | 57.07 | 4.73 | 11.80 |

EXAMPLE 32

β-[[2(S)-[[[4-(aminoiminomethyl)phenyl]amino]carbonyl]-amino-3-(naphthyl-2)-propanoyl]amino]-propanoic acid; FAB-MS: MH+=448.
Elemental analysis: $C_{24}H_{25}N_5O_4 \cdot CF_3COOH$

|  | C | H | N |
|---|---|---|---|
| Calculated: | 55.61 | 4.81 | 12.47 |
| Found: | 57.00 | 4.45 | 12.66 |

EXAMPLE 33

Ethyl β-[[3-[[[[4-(aminoiminomethyl)phenyl]amino]carbonyl]-amino]phenyl-propanoyl]amino]-propanoate; FAB-MS: MH+=426.

EXAMPLE 34

β-[[3-[[[[4-(aminoiminomethyl)phenyl]amino]carbonyl] amino]-phenyl-propanoyl]amino]-propanoic acid; FAB-MS: MH+=398.
Elemental analysis: $C_{14}H_{19}N_5O_4 \cdot H_2O \cdot HCl$

|  | C | H | N |
|---|---|---|---|
| Calculated: | 53.15 | 5.80 | 15.50 |
| Found: | 51.01 | 5.38 | 15.15 |

EXAMPLE 35

Ethyl β-[[3-[[[[4-(aminoiminomethyl)phenyl]amino]carbonyl]-amino](3-hydroxy-phenyl)propanoyl]amino]-propanoate; FAB-MS: MH+=442.

EXAMPLE 36

β-[[3-[[[[4-(aminoiminomethyl)phenyl]amino]carbonyl]amino](3-hydroxyphenyl)-propanoyl]amino]-propanoic acid; FAB-MS: MH+=414.

Elemental analysis: $C_{20}H_{23}N_5O_5 \cdot 2H_2O \cdot HCl$

|  | C | H | N |
|---|---|---|---|
| Calculated: | 49.43 | 5.81 | 14.41 |
| Found: | 48.67 | 5.18 | 14.15 |

EXAMPLE 37

Ethyl β-[[3-[[[[4-(aminoiminomethyl)phenyl]amino]carbonyl]-amino](3-methoxy-phenyl)propanoyl]amino]-propanoate; FAB-MS: MH+=456.

EXAMPLE 38

β-[[3-[[[[4-(aminoiminomethyl)phenyl]amino]carbonyl]amino](3-methoxyphenyl)-propanoyl]amino]-propanoic acid; FAB-MS: MH+=428.

Elemental analysis: $C_{21}H_{25}N_5O_5 \cdot 1.5H_2O \cdot HCl$

|  | C | H | N |
|---|---|---|---|
| Calculated: | 51.37 | 5.95 | 14.27 |
| Found: | 50.78 | 6.08 | 13.89 |

EXAMPLE 39

Ethyl β-[[3-[[[[4-(aminoiminomethyl)phenyl]amino]carbonyl]-amino](2-methoxyphenyl)propanoyl]amino]-propanoate; FAB-MS: MH+=456.

EXAMPLE 40

β-[[3-[[[[4-(aminoiminomethyl)phenyl]amino]carbonyl]amino](2-methoxyphenyl)-propanoyl]amino]-propanoic acid; FAB-MS: MH+=428.

Elemental analysis: $C_{21}H_{25}N_5O_5 \cdot H_2O \cdot HCl$

|  | C | H | N |
|---|---|---|---|
| Calculated: | 52.33 | 5.86 | 14.53 |
| Found: | 50.65 | 5.28 | 14.05 |

EXAMPLE 41

Ethyl β-[[3-[[[[4-(aminoiminomethyl)phenyl]amino]carbonyl]-amino](4-ethyl-phenyl)propanoyl]amino]-propanoate; FAB-MS: MH+=454.

EXAMPLE 42

β-[[3-[[[[4-(aminoiminomethyl)phenyl]amino]carbonyl]amino](4-ethylphenyl)-propanoyl]amino]-propanoic acid; FAB-MS: MH+=426.

Elemental analysis: $C_{22}H_{27}N_5O_4 \cdot H_2O \cdot 1.5HCl$

|  | C | H | N |
|---|---|---|---|
| Calculated: | 53.03 | 6.17 | 14.06 |
| Found | 53.39 | 5.73 | 13.97 |

Example 43
Ethyl β-[[3-[[[[4-(aminoiminomethyl)phenyl]amino]carbonyl]-amino](4-chloro-phenyl)propanoyl]amino]-propanoate; FAB-MS: MH+=460.

Example 44
β-[[-3-[[[[4-(aminoiminomethyl)phenyl]amino]carbonyl]amino](4-chlorophenyl) -propanoyl]amino]-propanoic acid; FAB-MS: MH+=432.

Elemental analysis: $C_{20}H_{22}N_5O_4Cl \cdot HCl$

|  | C | H | N |
|---|---|---|---|
| Calculated: | 51.29 | 4.95 | 14.95 |
| Found | 48.76 | 4.61 | 14.12 |

EXAMPLE 45

Ethyl β-[[3-[[[[4-(aminoiminomethyl)phenyl]amino]carbonyl]-amino](4-nitro-phenyl)propanoyl]amino]-propanoate; FAB-MS: MH+=471.

EXAMPLE 46

β-[[3-[[[[4-(aminoiminomethyl)phenyl]amino]carbonyl]amino](4-nitrophenyl)-propanoyl]amino]-propanoic acid; FAB-MS: MH+=443.

Elemental analysis: $C_{20}H_{22}N_6O_6 \cdot HCl \cdot H_2O$

|  | C | H | N |
|---|---|---|---|
| Calculated: | 48.30 | 5.07 | 16.98 |
| Found: | 46.88 | 4.68 | 16.25 |

EXAMPLE 47

Ethyl β-[[3-[[[[4-(aminoiminomethyl)phenyl]amino]carbonyl]-amino](2-nitro-phenyl)propanoyl]amino]-propanoate; FAB-MS:-MH+=471.

EXAMPLE 48

β-[[3-[[[[4-(aminoiminomethyl)phenyl]amino]carbonyl]amino](2-nitrophenyl)-propanoyl]amino]-propanoic acid; FAB-MS: MH+=443.

Elemental analysis: $C_{20}H_{22}N_6O_6 \cdot HCl \cdot H_2O$

|  | C | H | N |
|---|---|---|---|
| Calculated: | 48.30 | 5.07 | 16.98 |
| Found: | 47.79 | 4.59 | 16.51 |

EXAMPLE 49

Ethyl β-[[3-[[[[4-(aminoiminomethyl)phenyl]amino]carbonyl]-amino](3-nitro-phenyl)propanoyl]amino]-propanoate; FAB-MS: MH+=471.

EXAMPLE 50

β-[[3-[[[[4-(aminoiminomethyl)phenyl]amino]carbonyl]amino](3-nitrophenyl)-propanoyl]amino]-propanoic acid; FAB-MS: MH+=443.

Elemental analysis: $C_{20}H_{22}N_6O_6 \cdot HCl \cdot H_2O$

|  | C | H | N |
|---|---|---|---|
| Calculated: | 48.30 | 5.07 | 16.98 |
| Found: | 46.50 | 4.70 | 16.08 |

EXAMPLE 51

Ethyl β(S)-[[[[[4(aminoiminomethyl)phenyl]amino]-carbonyl]aminoacetyl]amino]-3-pyridinepropanoate; FAB-MS: MH+=413.

Elemental analysis: $C_{20}H_{24}N_6O_4 \cdot 2HCl \cdot 1.7H_2O$

|  | C | H | N |
|---|---|---|---|
| Calculated: | 46.55 | 5.74 | 16.29 |
| Found: | 46.25 | 5.33 | 16.16 |

EXAMPLE 52

β(S)-[[[[[4-(aminoiminomethyl)phenyl]amino]carbonyl]aminoacetyl]amino]-3-pyridinepropanoic acid; FAB-MS: MH+=385.

Elemental analysis: $C_{18}H_{20}N_6O_4$

|  | C | H | N |
|---|---|---|---|
| Calculated: | 46.04 | 5.08 | 16.96 |
| Found: | 47.32 | 5.56 | 15.56 |

EXAMPLE 53

Ethyl β-[[[[[4-(aminoiminomethyl)phenyl]amino]carbonyl]aminoacetyl]amino]-4-chlorophenylpropanoate; FAB-MS: MH+=460.

EXAMPLE 54

β-[[[[[4-(aminoiminomethyl)phenyl]amino]carbonyl]aminoacetyl]-amino]-4-chlorophenylpropanoic acid; FAB-MS: MH+=432.

Elemental analysis: $C_{20}H_{22}N_5O_4Cl \cdot 2HCl$

|  | C | H | N |
|---|---|---|---|
| Calculated: | 47.58 | 4.79 | 13.87 |
| Found: | 47.34 | 4.82 | 13.39 |

EXAMPLE 55

β-[[[[[4-(aminoiminomethyl)phenyl]amino]carbonyl]aminoacetyl]amin o]-glutaric acid. FAB-MS: MH+=366.
Elemental analysis: $C_{15}H_{19}N_5O_6 \cdot HCl \cdot 10LiCl$

|  | C | H | N |
|---|---|---|---|
| Calculated: | 21.81 | 2.44 | 8.48 |
| Found: | 21.22 | 2.32 | 8.02 |

The platelet-binding inhibitor activity of the compounds of the present invention can be demonstrated by the assays presented below.

IN-VITRO PLATELET AGGREGATION IN PRP

Healthy male or female dogs were fasted for 8 hours prior to drawing blood; then 30 ml whole blood was collected using a butterfly needle and 30 cc plastic syringe with 3 ml of 0.129M buffered sodium citrate (3.8%). The syringe was rotated carefully as blood was drawn to mix the citrate. Platelet-rich plasma (PRP) was prepared by centrifugation at 975×g for 3.17 minutes at room temperature allowing the centrifuge to coast to a stop without braking. The PRP was removed from the blood with a plastic pipette and placed in a plastic capped, 50 mL Corning conical sterile centrifuge tube which was held at room temperature. Platelet poor plasma (PPP) was prepared by centrifuging the remaining blood at 2000×g for 15 minutes at room temperature allowing the centrifuge to coast to a stop without braking. The PRP was adjusted with PPP to a count of $2-3 \times 10^8$ platelets per mL. 400 uL of the PRP preparation and 50 uL of the compounds solution to be tested or saline were preincubated for i minute at 37° C. in a BioData, Horsham, Pa.). 50 uL of adenosine 5' diphosphate (ADP) (50 um final concentration) was added to the cuvettes and the aggregation was monitored for 1 minute. All compounds are tested in duplicate. Results are calculated as follows: Percent of control=[ (maximal OD minus initial OD of compound) divided by (maximal OD minus initial OD of control saline)]×100. The % inhibition=100−(percent of control).

The compounds tested and their median inhibitory concentrations ($IC_{50}$) are recorded in Table I. $IC_{50}$'s (dosage at which 50% of platelet aggregation is inhibited) were calculated by linear regression of the dose response curve. The assay results for the compounds of Examples 1 to 14 are set forth in Table I below.

INHIBITION OF EX VIVO COLLAGEN INDUCED AGGREGATION BY COMPOUNDS OF THE INVENTION

The purpose of this assay is to determine the effects of antiplatelet compounds on ex vivo collagen induced platelet aggregation when administered either intravenously or orally to dogs.

Pretreatment (control) blood samples are drawn from either conscious or anesthetized dogs (Beagles) and centrifuged to prepare platelet rich plasma (PRP). Aggregatory response to collagen is measured in a aggregometer and used as Control. Compounds are administered, either intragasterically (either by capsule or stomach tube or intravenously). Blood samples are drawn at predetermined intervals after compound administration. PRP prepared and aggregation to collagen determined. Compound inhibition of aggregation is determined by comparing the aggregation response after compound administration to the pretreatment response.

TABLE I

| Example | Dog PRP $IC_{50}$ or % Inh | Ex Vivo Effect after IG Administration |
|---|---|---|
| 1 | NT | + |
| 2 | $3.3 \times 10^{-7}$M | NT |
| 3 | NT | + |
| 4 | $2.6 \times 10^{-7}$M | NT |
| 5 | NT | NT |
| 6 | 5% at $10^{-5}$M | NT |
| 7 | NT | NT |
| 8 | $4.9 \times 10^{-6}$M | NT |
| 9 | NT | NT |

TABLE I-continued

| Example | Dog PRP IC$_{50}$ or % Inh | Ex Vivo Effect after IG Administration |
|---|---|---|
| 10 (isomer 1) | 9% at 10$^{-5}$M | NT |
| 10 (isomer 2) | * | NT |
| 11 | NT | NT |
| 12 | 6.0 × 10$^{-6}$M | NT |
| 13 | NT | NT |
| 14 (isomer 1) | 2.0 × 10$^{-6}$M | NT |
| 14 (isomer 2) | * | NT |

NT - not tested
* - not active at the dose tested

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound or a pharmaceutically acceptable salt, thereof having the formula:

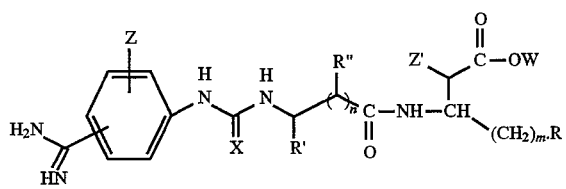

wherein R is selected from the group consisting of hydrogen, lower alkyl radicals, lower alkenyl radicals, lower alkynyl radicals, alicyclic hydrocarbon radicals, and aromatic hydrocarbon radicals, wherein all of said radicals are optionally substituted with hydroxyl, lower alkoxy, lower alkyl, halogen, nitro, carboxyl, trifluoromethyl, amino, acyloxy, phenyl and naphthyl which are optionally substituted with halogen, nitro, lower alkoxy, and lower alkyl;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

Z, Z' are independently selected from the group consisting of hydrogen, lower alkyl radicals, halogen, alkoxy, cyano, sulfonyl, and hydroxy radicals;

X is selected from the group consisting of oxygen, sulfur or nitrogen radicals, wherein nitrogen radicals may be substituted with hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

R', R" are independently selected from the group consisting of hydrogen, lower alkyl radicals, and monocyclic or bicyclic aromatic hydrocarbon radicals wherein all of said radicals are optionally substituted with hydroxyl, lower alkyl, lower alkoxy, halogen, nitro, or amino.;

m is an integer from 0 to about 6; and n is an integer 0 to about 3.

2. A compound according to claim 1 wherein R is selected from the group consisting of hydrogen, lower alkyl radicals of 1 to about 6 carbon atoms, lower alkenyl radicals of 2 to about 6 carbon atoms, lower alkynyl radicals of 2 to about 8 carbon atoms, alicyclic hydrocarbon radicals of 3 to about 6 carbon atoms, and aromatic hydrocarbon radicals, wherein all of said radicals are optionally substituted with hydroxyl, lower alkoxy, lower alkyl, halogen, nitro, carboxyl, and trifluoromethyl;

W is selected from the group consisting of hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, alkoxy, cyano, sulfonyl, lower alkyl and hydroxy radicals;

X is selected from the group consisting of oxygen, sulfur or nitrogen radicals, wherein nitrogen radicals may be substituted with hydrogen, lower alkyl radicals, lower alkenyl radicals, lower alkynyl radicals, alicyclic hydrocarbon radicals and aromatic hydrocarbon radicals;

R', R" are independently selected from the group consisting of hydrogen, lower alkyl radicals, and aromatic carbon radicals wherein all of said radicals are optionally substituted with hydroxyl, lower alkyl, lower alkoxy, halogen, nitro, or amino;

m is an integer from 0 to about 3; and n is an integer 0 to about 2.

3. A compound according to claim 1 wherein R is selected from the group consisting of hydrogen, lower alkyl radicals, phenyl radicals, and substituted phenyl radicals wherein each radical is optionally substituted with lower alkyl, halogen, and carboxyl;

W is selected from the group consisting of hydrogen and lower alkyl radicals;

Z, Z' are independently selected from the group consisting of hydrogen, halogen, alkoxy, and lower alkyl radicals;

X is selected from the group consisting of oxygen, sulfur or nitrogen radicals, wherein nitrogen radicals may be substituted with hydrogen, lower alkyl radicals, and alicyclic hydrocarbon radicals;

R', R" are independently selected from the group consisting of hydrogen, lower alkyl radicals, and aromatic carbon radicals wherein all of said radicals are optionally substituted with hydroxyl, lower alkyl, lower alkoxy, halogen, and nitro;

m is an integer from 0 to about 2; and n is an integer 0 to about 1.

4. A compound according to claim 1 selected from the group consisting of:

ethyl β-[[3-[[[4-(aminoiminomethyl)phenyl]amino]-N-methylcarbonylimide]aminopropanoyl]amino]propanoate;

β-[[3-[[[4-(aminoiminomethyl)phenyl]amino]-N-methylcarbonylimide]aminopropanoyl]amino]propanoic acid;

ethyl β-[[3-[[4-(aminoiminomethyl)phenyl]amino]thiocarbonyl]aminopropanoyl]-amino]propanoate;

β-[[3-[[[4-(aminoiminomethyl)phenyl]-amino]thiocarbonyl]aminopropanoyl]-amino]propanoic acid;

ethyl β-[[3-[[4-(aminoiminomethyl)phenyl]-amino]carbonyl]aminopropanoyl]amino]propanoate;

β-[[3-[[[4-(aminoiminomethyl)phenyl]amino]-carbonyl]aminopropanoyl]amino]propanoic acid;

ethyl β-[[2(S)-[[[4-(aminoiminomethyl)phenyl]-amino]carbonyl]amino-3-(naphthyl-2)propanoyl]amino]propanoate;

β-[[2(S)-[[[4-(aminoiminomethyl)phenyl]amino]carbonyl]amino-3-(naphthyl-2)-propanoyl]amino]propanoic acid;

ethyl β-[[3-[[[[4-(aminoiminomethyl)phenyl]-amino]carbonyl]amino]phenylpropanoyl]amino]-propanoate;

β-[[3-[[[[4-(aminoiminomethyl)phenyl]amino]carbonyl]amino]phenylpropanoyl]amino]propanoic acid;

ethyl β-[[3-[[[[4-(aminoiminomethyl)phenyl]amino]carbonyl]amino](3-hydroxyphenyl) propanoyl]amino]propanoate;

β-[[3-[[[[4-(aminoiminomethyl)phenyl]amino]carbonyl]amino](3-hydroxphenyl)propanoyl]amino]-propanoic acid;

ethyl β-[[3-[[[[4-(aminoiminomethyl)phenyl]amino]carbonyl]amino](3-methoxyphenyl)propanoyl]amino]propanoate;

β-[[3-[[[[4-(aminoiminomethyl)phenyl]amino]carbonyl]amino](3-methoxyphenyl)propanoyl]amino]propanoic acid;

ethyl β-[[3-[[[[4-(aminoiminomethyl)phenyl]amino]carbonyl]amino](2-methoxyphenyl)propanoyl]amino]propanoate;

β-[[3-[[[[4-(aminoiminomethyl)phenyl]amino]carbonyl]amino](2-methoxyphenyl)propanoyl]amino]propanoic acid;

ethyl β-[[3-[[[[4-(aminoiminomethyl)phenyl]amino]carbonyl]amino](4-ethylphenyl)propanoyl]amino]propanoate;

β-[[3-[[[[4-(aminoiminomethyl)phenyl]amino]carbonyl]amino](4-ethylphenyl)propanoyl]amino]-propanoic acid;

ethyl β[[3-[[3-[[[[4-(aminoiminomethyl)phenyl]amino]carbonyl]amino](4-chlorophenyl)propanoyl]amino]-propanoate;

β-[[-3-[[[[4-(aminoiminomethyl)phenyl]amino]carbonyl]amino](4-chlorophenyl)propanoyl]amino]propanoic acid;

ethyl β-[[3-[[[[4-(aminoiminomethyl)phenyl]amino]carbonyl]amino](4-nitrophenyl)propanoyl]amino]propanoate;

β-[[3-[[[[4-(aminoiminomethyl)phenyl]amino]carbonyl]amino](4-nitrophenyl)propanoyl]amino]propanoic acid;

ethyl β-[[3-[[[[4-(aminoiminomethyl)phenyl]amino]carbonyl]amino](2-nitrophenyl)propanoyl]amino]propanoate;

β-[[3-[[[[4-(aminoiminomethyl)phenyl]amino]carbonyl]amino](2-nitrophenyl)-propanoyl]amino]propanoic acid;

ethyl β-[[3-[[[[4-(aminoiminomethyl)phenyl]amino]carbonyl]amino](3-nitrophenyl)propanoyl]amino]propanoate;

β-[[3-[[[[4-(aminoiminomethyl)phenyl]amino]carbonyl]amino](3-nitrophenyl)propanoyl]amino]propanoic acid;

ethyl β-[[[[[4-(aminoiminomethyl)phenyl]amino]carbonyl]aminoacetyl]amino]-4-chlorophenylpropanoate;

β-[[[[[4-(aminoiminomethyl)phenyl]amino]carbonyl]aminoacetyl]-amino]-4-chlorophenylpropanoic acid; and β-[[[[[4-(aminoiminomethyl)phenyl]amino]]carbonyl]aminoacetyl]amino]glutaric acid.

5. A compound or a pharmaceutically acceptable salt thereof having the formula

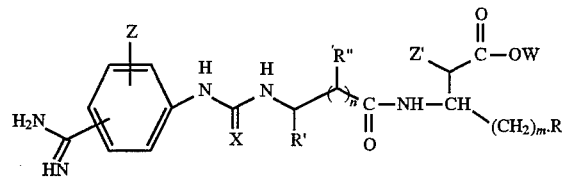

wherein R is hydrogen;

W is selected from the group consisting of hydrogen, and lower alkyl radicals;

Z, Z' are hydrogen;

X is selected from the group consisting of oxygen, sulfur or nitrogen radicals, wherein nitrogen radicals may be substituted with hydrogen, and lower alkyl radicals;

R', R" are independently selected from the group consisting of hydrogen, lower alkyl radicals and monocyclic or bicyclic aromatic hydrocarbon radicals;

m is 0 to about 1; and n is an integer 0 to about 1.

6. A pharmaceutical composition comprising at least one non-toxic pharmaceutically acceptable carrier and at least one compound according to claim 1 together with said carrier.

7. A pharmaceutical composition as recited in claim 6 comprising at least one non-toxic pharmaceutically acceptable carrier and at least one compound according to claim 2 or 3 together with said carrier.

8. A method of treating a mammal to inhibit platelet aggregation comprising administering a therapeutically effective amount of at least one compound of claim 1 to a mammal in need of such treatment.

9. A method of treating a mammal to inhibit platelet aggregation as recited in claim 8 comprising administering a therapeutically effective amount of at least one compound of claim 2 or 3 to a mammal in need of such treatment.

* * * * *